United States Patent [19]
Waldbillig

[11] 3,940,408
[45] Feb. 24, 1976

[54] 2-AMINO-5-HYDROCARBYLDITHIO-1,3,4-THIADIAZOLE COMPOUNDS

[75] Inventor: James O. Waldbillig, Wappingers Falls, N.Y.

[73] Assignee: Texaco Inc., New York, N.Y.

[22] Filed: Sept. 9, 1974

[21] Appl. No.: 504,640

Related U.S. Application Data

[62] Division of Ser. No. 445,384, Feb. 25, 1974, Pat. No. 3,869,395.

[52] U.S. Cl. ........................................... 260/306.8 D
[51] Int. Cl.[2] ........................................ C07D 285/12
[58] Field of Search .............. 260/306.8 D, 302.5 D

[56] References Cited
OTHER PUBLICATIONS
Lecher, Chem. Abstracts, Vol. 14, 3080 (1920).
Reid, Organic Chemistry of Bivalent Sulfur, Vol. I, Chemical Pub., N.Y., 1958, pp. 273–275.

Primary Examiner—Richard J. Gallagher
Attorney, Agent, or Firm—T. H. Whaley; C. G. Ries; Robert A. Kulason

[57] ABSTRACT

Thiadiazole derivatives characterized by the formula:

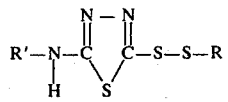

where R is hydrocarbyl of from 1 to 30 carbons and R' is hydrogen or hydrocarbyl of from 1 to 30 carbons prepared by the method of contacting a 2-amino-5-mercapto-1,3,4-thiadiazole characterized by the formula:

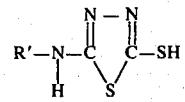

sequentially with an alkali metal hydroxide and a hydrocarbyl sulfenyl bromide characterized by the formula R-S-Br where R and R' are as heretofore defined. Hydrocarbon oil compositions comprising a hydrocarbon oil of lubricating viscosity containing between about 0.01 and 50 wt. % of said amino hydrocarbyldithio thiadiazole.

4 Claims, No Drawings

2-AMINO-5-HYDROCARBYLDITHIO-1,3,4-THIADIAZOLE COMPOUNDS

This is a division, of application Ser. No. 445,384 filed Feb. 25, 1974, now U.S. Pat. No. 3,869,395.

BACKGROUND OF INVENTION

In the internal combustion engines of today as well as mechanisms associated therewith such as automatic transmissions, a substantial amount of copper is employed in the construction thereof. However, some of the most commonly used additives in lubricating oil compositions servicing the internal combustion systems, e.g., gear oils, are highly corrosive to copper. Specifically, among the most effective agents which have been developed for compounding with lubricants to improve extreme pressure and wear properties are sulfur containing organic compounds, for example, sulfurized triisobutylene and sulfurized diisobutylene, sulfurized terpene, sulfurized hydrocarbon oils, vegetable oils, animal oils, xanthate esters, organic polysulfides, particularly polyalkyl polysulfides which contain active sulfur or sulfur compounds. These wear and extreme pressure agents are corrosive to copper. In addition, those hydrocarbon oils derived from high sulfur containing crude oils wherein the sulfurous components are not thoroughly removed in refining are often corrosive to copper.

To solve this problem of copper corrosion, the prior art employs various copper corrosion inhibitors with varying degree of effectiveness. One such class of inhibitors are disclosed in U.S. Pat. Nos. 2,719,125 and 2,719,126 which are directed to copper corrosion inhibited lubricating oil compositions containing as the copper corrosion inhibitor a 1,3,4-thiadiazole polysulfide characterized by the formula:

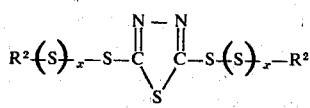

where $R^2$ is a hydrocarbon radical (hydrocarbyl) such as alkyl of from 1 to 30 carbons and x is an integer of from 0 to 8. It is interesting to note that the fact that this particular sulfurous material is an effective copper corrosion inhibitor whereas the other aforementioned sulfur (compounds) of antiwear and extreme pressure properties are corrosive to copper, indicates the unpredictability regarding the function of sulfur compounds as copper corrosion inhibiting agents in the lube oil art.

SUMMARY OF INVENTION

I have discovered and this constitutes one aspect of my invention a new class of sulfur compounds which are effective in inhibiting the corrosion of copper by copper corrosive hydrocarbon oil formulations. Another aspect of my invention are hydrocarbon oil formulations containing the novel sulfur compounds. More particularly, the instant invention relates to a 2-amino-5-hydrocarbyldithio-1,3,4-thiadiazole characterized by the formula:

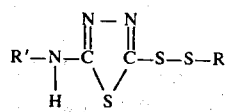

where R is hydrocarbyl of from 1 to 30 carbons and R' is hydrogen or hydrocarbyl of from 1 to 30 carbons. In addition, the invention specifically relates to concentrate and finished hydrocarbon oil compositions comprising a hydrocarbon oil of lubricating viscosity and said amino hydrocarbyldithio thiadiazole.

DETAILED DESCRIPTION OF THE INVENTION

Specifically, the amino hydrocarbyldithio thiadiazole compounds of the invention are prepared by first reacting thiosemicarbazide of the formula:

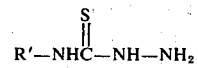

where R' is hydrogen or hydrocarbyl, i.e., alkyl, aryl, alkaryl and aralkyl of from 1 to 30 carbons, with carbon disulfide to form 2-amino-5-mercapto-1,3,4-thiadiazole characterized by the formula:

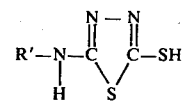

where R' is as heretofore defined. The reaction is carried out at a temperature between about 20° and 200°C. utilizing a mole ratio of the thiosemicarbazide to carbon disulfide of between about 1:10 and 4:1. Further description of the 2-amino-5-mercapto-1,3,4-thiadiazole product can be found in U.S. Pat. No. 2,389,126.

The formed 2-amino-5-mercapto-1,3,4-thiadiazole is then contacted with an alkali metal hydroxide such as sodium hydroxide and potassium hydroxide at a temperature between about −20° and 100°C. utilizing a mole ratio of thiadiazole to alkali metal hydroxide of between about 2:1 and 1:1.1 to form the alkali metal mercaptide intermediate characterized by the formula:

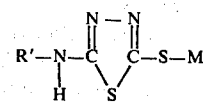

where M is the alkali metal moiety and R' is as heretofore defined.

The intermediate mercaptide salt is contacted with a hydrocarbyl sulfenyl bromide characterized by the formula R-S-Br where R is hydrocarbyl, i.e., alkyl, aryl, alkaryl or aralkyl of from 1 to 30 carbons. The reaction is conducted at a temperature between about −50 and 50°C. utilizing a mole ratio of thiadiazole reactant to hydrocarbyl sulfenyl bromide of between about 1.1:1 and 1:1.1. The sulfenyl bromide reactant is prepared by reacting hydrocarbyl mercaptan e.g. alkyl mercaptan with bromine at temperatures between about −50 and 50°C. utilizing a mole ratio of mercaptan to bromine of between about 2:1 and 1:20.

In the foregoing described reactions, liquid diluents are advantageously employed, e.g., in amounts of between about 25 and 95 wt. % of the reaction mixture. Examples of such diluents are benzene dimethylformamide, mixtures of benzene and dimethylformamide, toluene o, m, and p-xylene and mixtures thereof, N,N-diethylformamide, N,N-dimethylacetamide, diglyme (diethylene glycol dimethyl ether), chlorobenzene, carbon tetrachloride, hexachloroethane, ethylene glycol dimethyl ether. In most instances a single solvent will not be suitable for all stages thus normally requiring the use of several different solvents.

All stages of the reaction are preferably conducted in an inert atmosphere such as nitrogen.

Examples of the thiosemicarbazide reactants contemplated herein are thiosemicarbazide, 4-ethyl-3-thiosemicarbazide, 4-propyl-3-thiosemicarbazide, 4-butyl-3-thiosemicarbazide, 4-pentyl-3-thiosemicarbazide, 4-hexyl-3-thiosemicarbazide, 4-heptyl-3-thiosemicarbazide, 4(2-ethylhexyl)-3-thiosemicarbazide, 4-tert-octyl-3-thiosemicarbazide, 4-dodecyl-3-thiosemicarbazide, 4-tetradecyl-3-thiosemicarbazide, and 4-octadecyl-3-thiosemicarbazide, 4-methyl-3-thiosemicarbazide, 4-phenyl-3-thiosemicarbazide, 4-benzyl-3-thiosemicarbazide, 4-tolyl-3-thiosemicarbazide, 4-naphthyl-3-thiosemicarbazide.

Examples of the amino mercapto thiadiazoles contemplated herein are

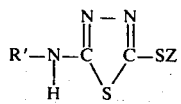

where R' and Z are hydrogen where R' is ethyl and Z is hydrogen; where R' is hydrogen and Z is potassium; where R' is ethyl and Z is potassium; where R' is hydrogen and Z is sodium, where R' is methyl and Z is potassium; where R' is tert-octyl and Z is potassium; where R' is dodecyl and Z is sodium; where R' is octadecyl and Z is sodium; where R' is tolyl and Z is potassium; where R' is phenyl and Z is sodium; where R' is naphthyl and Z is potassium and where R' is benzyl and Z is sodium.

Examples of the hydrocarbyl sulfenyl reactants are t-dodecyl sulfenyl bromide, t-octyl sulfenyl bromide, Z-methyl-2-butyl sulfenyl bromide, 3-methyl-1-butyl sulfenyl bromide, n-pentyl sulfenyl bromide, n-octyl sulfenyl bromide, n-dodecyl sulfenyl bromide, n-octadecyl sulfenyl bromide, tolyl sulfenyl bromide, naphthyl sulfenyl bromide, phenyl sulfenyl bromide and benzyl sulfenyl bromide.

Examples of the amino hydrocarbyldithio thiadiazole products contemplated herein are 2-amino-5-t-dodecyldithio-1,3,4-thiadiazole; 2-ethylamino-5-t-octyldithio-1,3,4-thiadiazole; 2-amino-5-t-octyldithio-1,3,4-thiadiazole; 2-amino-5-n-octadecyldithio-1,3,4-thiadiazole; 2-ethylamino-5-n-octadecyldithio-1,3,4-thiadiazole; 2-(2-ethylhexyl)amino-5-n-dodecyldithio-1,3,4-thiadiazole; 2-(2-ethylhexyl)amino-5-n-octyldithio-1,3,4-thiadiazole; 2-naphthyl-5-octyldithio-1,2,3-thiadiazole; 2-benzyl-5-pentyldithio-1,3,4-thiadiazole; 2-amino-5-phenyldithio-1,3,4-thiadiazole and 2-amino-5-tolyldithio-1,3,4-thiadiazole.

In regard to the finished compositions of the present invention, the amino hydrocarbyldithio thiadiazole products are employed in hydrocarbon base oil in copper corrosion inhibiting amounts, e.g., from between about 0.01 and 10 wt. %, preferably between about 0.05 and 1 wt. %. The hydrocarbon base oil in the finished composition normally constitutes at least about 85 wt. % of said composition, preferably about 90 wt. % or more. Hereinbefore and hereinafter by the term "finished" it is intended to denote that the composition is in a state ready for ultimate use without need for further dilution with base oil.

In the concentrate compositions contemplated to which additional hydrocarbon oil is added to form the finished compositions, the concentrate form being preferably for storage and transport, the hydrocarbon base oil normally constitutes at least about 50 wt. %, preferably between about 50 and 90 wt. % and the amino hydrocarbyldithio thiadiazole between about 10 and 50 wt. % of the concentrate formulation.

Thus, concentrate and finished compositions are contemplated ranging from at least about 50 wt. % hydrocarbon oil and between about 0.01 and 50 wt. % amino hydrocarbyldithio thadiazole additive.

The hydrocarbon oil components employed in the finished and concentrate formulations of the invention advantageously are mineral lubricating oils such as paraffinic lube oil, naphthenic lube oil and mixtures thereof. Other suitable hydrocarbon oils are those synthetically formed such as the polyalkylene, e.g., polyisobutylene of a molecular weight of from about 1000 to 5000. The viscosity of the base oils employed will be dependent upon the particular use intended for the finished formulation. However, the viscosity of oil employed will generally range between about 70 and 5000 SUS at 100°F.

In addition to the hydrocarbon oil and amino hydrocarbyldithio thiadiazole components in the contemplated oil compositions, other additives are normally employed, the particular other additives utilized being dependent on the specific service intended for the finished compositions of the invention. Some of the other additives contemplated belong in classes of detergent-dispersants, pour depressants, VI improvers, extreme pressure agents, antiwear agents, anti-oxidants, supplementary corrosion inhibitors and antifoamants.

Examples of the extreme pressure and antiwear agents are dithiolethione derived from sulfurizing triisobutylene and alkyl sulfides, disulfides and polysulfides prepared by sulfurization of isobutylene with sulfur dichloride. Other extreme pressure and antiwear agents contemplated are the sulfurized terpenes, sulfurized hydrocarbon oils and polyalkyl polysulfides, all of which contain active sulfur or sulfur compounds which are corrosive to copper. These extreme pressure and antiwear agents are normally present in the finished formulations (when utilized) in amounts of between about 0.1 and 10 wt. %, preferably between 0.05 and 5 wt. %.

When detergent-dispersants are employed, they are usually utilized in amounts between about 0.5 and 5 wt. %. Examples of ashless dispersants are alkenyl succinimides characterized by the general formula:

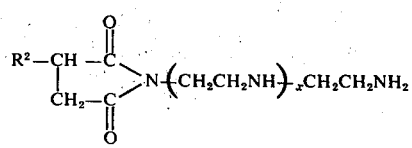

where $R^2$ is monoolefinic aliphatic hydrocarbon of from about 50 to 200 carbons and x is an integer of from about 1 to 10, derived from alkenyl succinic anhydride and polyethylene polyamines. Particularly suitable derivatives are the diethylene triamine, triethylene tetramine, tetraethylene pentamine derivatives of polyisobutylene succinic anhydride, particularly where R is of a molecular weight between about 700 and 2000, e.g., about 1300. These ashless dispersants are further described in U.S. Pat. Nos. 3,172,892 and 3,202,678. The non ashless dispersants which may be utilized are the alkaline earth metal overbased calcium alkaryl sulfonates such as calcium carbonate overbased calcium alkaryl sulfonate wherein the alkaryl sulfonate moiety is of a molecular weight of 500 to 1000. These overbased sulfonates are further described in U.S. Pat. Nos. 3,027,325, 3,312,618 and 3,537,996.

Examples of the contemplated viscosity index improvers which in many instances also function as pour depressors are the methacrylate ester polymers characterized by the general formula:

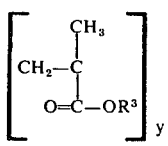

where $R^3$ is an alkyl group, a dimethylamino group or mixtures of said groups containing from 1 to 20 carbons and y is an integer providing a molecular weight of the polymer in the range of 25,000 to 1,250,000, preferably 50,000 to 500,000. Methacrylate ester polymers possessing pour point depressant as well as viscosity index improving properties are well known, e.g., U.S. Pat. No. 2,737,496. A very effective material of this type is the tetrapolymer of butyl, lauryl, stearyl and dimethylaminoethyl methacrylate in approximate ratios of 1:2:1:0.2. The methacrylate ester is advantageously employed in the base oils in amounts ranging from 0.1 to 10 wt. %, preferably about 0.2 to 5 wt. %, in order to impart the desired viscosity index and/or pour point thereto.

Examples of suitable antioxidants which also function as supplementary corrosion inhibitors are the aryl substituted amine compounds exemplified by phenylnaphthylamine as well as compounds such as phenylenediamine, phenathiazine, diphenylamines employed in amounts between about 0.1 and 5 wt. %. Some of the preferred compounds are the phenyl-alphanaphthylamines and a mixture of 2,2-diethyl-4,4'-t-dioctyldiphenyleneamine and 2,2'-diethyl-4,6-diphenylamine.

Additional examples of antioxidants are the hydrocarbyl dithiophosphates. Particularly effective compound in this class are zinc di(nonylphenoxyethyl) dithiophosphate, zinc di(dodecylphenoxyethyl) dithiophosphate and zinc di(nonylphenoxythoxyethyl) dithiophosphate prepared by reacting nonyl phenol and ethylene oxide compounds with phosphorus pentasulfide followed by neutralization of the acid formed with basic zinc compound such as zinc carbonate, zinc oxide or zinc hydroxide. The general preparation and description of the compounds in this class are disclosed in U.S. Pat. Nos. 2,344,395 and 3,293,181.

Examples of additional supplemental corrosion inhibitors are oleyl amine and ethyloleyl acid phosphate.

Antifoamants which are suitable for use are the silicone polymers such as polymeric dimethyl silicone.

The following examples further illustrate the invention but are not to be construed as limitations thereof.

EXAMPLE I

This example illustrates the preparation of 2-amino-5-mercapto-1,3,4-thiadiazole reactant.

To a solution of 45.5 grams (0.5 mole) of thiosemicarbazide in 1000 mls. of dimethylformamide there was charged 32 grams of carbon disulfide. The resultant solution was heated for 4 hours at 80°C. and then stripped to 93°C. under reduced pressure of 0.15 mm Hg. The residue was slurried with 250 mls. of benzene followed by removal of the benzene via distillation. The residue product was recrystallized from 250 mls. of methanol-ethanol mixture (Formula 30) to yield 28 grams (42 wt. %) of product which was analyzed and found to be 2-amino-5-mercapto-1,3,4-thiadiazole having an elemental analysis of 31.7 (calc. 31.6) wt. % nitrogen; 47.1 (48.1) wt. % sulfur; 19.2 (18.0) wt. % carbon and 2.1 (2.3) wt. % hydrogen.

EXAMPLE II

This example illustrates the preparation of 2-ethylamino-5-mercapto-1,3,4-thiadiazole reactant.

To a stirred solution of 11.9 grams (0.10 mole) of 4-ethyl-3-thiosemicarbazide and 700 mls. of dimethylformamide there were charged 8.4 grams (0.11 mole) of carbon disulfide. The reaction mixture was heated at 90°C. for 4 hours and stripped to 93°C. under reduced pressure of 0.04 mm Hg. The residual solid was recrystallized from absolute ethanol and analysis found it to be 2-ethylamino-5-mercapto-1,3,4-thiadiazole of an elemental analysis of 29.5 (calc. 29.8) wt. % carbon; 4.7 (4.4) wt. % hydrogen; 25.6 (26.1) wt. % nitrogen and 39.4 (39.7) wt. % sulfur.

EXAMPLE III

This example illustrates the preparation of a species of the product of the invention from a product of the type formed in Example I.

A solution of 5.6 grams (0.1 mole) of potassium hydroxide and 50 mls. of ethanol was added to a mixture of 13.3 grams (0.10 mole) of 2-amino-5-mercapto-1,3,4-thiadiazole in 200 mls. of diglyme (diethylene glycol dimethyl ether) at 0°C. There was added 100 mls. of benzene and the resultant mixture was heated to 49°C. on the rotary evaporator to remove benzene and ethanol leaving the potassium salt of 2-amino-5-mercapto-1,3,4-thiadiazole as residue.

A t-dodecyl sulfenyl bromide solution was prepared by adding 16 grams (0.10 mole) of bromine to a solution of 100 mls. of carbon tetrachloride and 20.2 grams (0.10 mole) t-dodecyl mercaptan at a temperature of about 0°C. The product was blown with nitrogen for a period of 2 hours.

The formed t-dodecyl sulfenyl bromide solution was added to the above formed potassium salt. The resultant product was stripped to 93°C. (0.15 mm Hg.), dissolved in 300 mls. of ether, and filtered through paper. The filtrate was washed twice with 300 mls. of 5 wt. % aqueous sodium carbonate and the resultant solution was dried over sodium sulfate and stripped to 93°C. under a reduced pressure of 0.125 mm Hg. The residual solid weighed 19 grams representing a yield of 57 wt. %. Analysis found it to be 2-amino-5-6-dodecyldithio-1,3,4-thiadiazole having an elemental analysis of 9.7 (calc. 12.6) wt. % nitrogen 26.2 (28.8) wt. % sulfur and 0.43 (0) wt. % bromine.

EXAMPLE IV

This example illustrates the preparation of still another species of the product of the invention.

A solution of 0.56 gram (0.01 mole) of potassium hydroxide in 25 mls. of anhydrous ethanol was added to 2-(ethylamino)-5-mercapto-1,3,4-thiadiazole in 100 mls. of diethylene glycol dimethyl ether at 0°C. under a nitrogen blanket. To the resultant mixture 15 mls. of benzene was added and the mixture was heated at 49°C. on a rotary evaporator to remove ethanol, benzene and water leaving residual solution of potassium salt of 2-(ethylamino)-5-mercapto-1,3,4-thiadiazole.

A t-octyl sulfenyl bromide-carbon tetrachloride solution was prepared by adding 1.76 grams (0.11 mole) bromine to a solution of 1.61 grams (0.11 mole) t-octyl mercaptan and 50 mls. carbon tetrachloride solution at 10° dropwise. The resultant mixture was stirred with nitrogen blowing for 2 hours at about 0°C.

The t-octyl sulfenyl bromide solution was added to the aforeformed residual solution at 0°C. The resultant product was filtered and stripped to 93°C. (0.1 mm Hg.). The product was then dissolved in 150 mls. of ether and washed twice with two 150 ml. portions of 5 wt. % aqueous sodium carbonate and then dried over sodium sulfate. The dried product was stripped to 93°C. (0.1 mm Hg.) leaving a solid residue of 2.3 grams which upon analysis was identified as 2-ethylamino-5-t-octyldithio-1,3,4-thiadiazole having an elemental analysis of 48 (calc. 47.2) wt. % carbon, 7.7 (7.5) wt. % hydrogen, 11.4 (13.8) wt. % nitrogen and 28.2 (31.5) wt. % sulfur.

EXAMPLE V

This example further illustrates the preparation of still another species of the product of the invention.

A solution of 28.05 (0.5) grams of potassium hydroxide in 200 mls. of ethanol was combined with 60 grams (0.45 mole) of 2-amino-5-mercapto-1,3,4-thiadiazole in 500 mls. of diethylene glycol dimethyl ether at 0°C. There was then added 200 mls. of benzene and the mixture was then stripped to 92°C. on a rotary evaporator removing 310 mls. of solvent leaving as residue the potassium salt of 2-amino-5-mercapto-1,3,4-thiadiazole.

A t-octyl sulfenyl bromide solution prepared by adding 80 grams (0.5 mole) bromine to 73 grams (0.50 mole) t-octyl mercaptan in 500 mls. carbon tetrachloride while blowing with nitrogen at about 0°C. followed by passage of nitrogen through the solution vigorously for 2 hours was added at 10°C. to the potassium salt residue. The resultant mixture was stirred at ambient temperature for 1 hour and then filtered. The solids were washed with ether and the combined organic phase was stripped to 93°C. on a rotary evaporator. There was recovered as residue 91.5 grams of a solid-liquid mixture. The product was dissolved in 500 mls. of ether and washed with two 500 ml. portions of 5 wt. % aqueous sodium carbonate. The washed product was dried over magnesium sulfate. Additional solids formed. The solids were removed and 200 mls. of pentane were added to the solution. The resultant solution was filtered and stripped to 93°C. (rotary evaporator) and the resultant product was solid. Analysis determined it to be 2-amino-5-t-octyldithio-1,3,4-thiadiazole having an elemental analysis of 14.8 (15.2) wt. % nitrogen and 34.4 (34.6) wt. % sulfur.

EXAMPLE VI

This example illustrates the lubricating oil compositions containing the amino hydrocarbyldithio thiadiazole product and the effectiveness of the amino hydrocarbyldithio thiadiazoles as copper corrosion inhibitors in said compositions.

The following is a description of the base oil formulations to which the amino hydrocarbyldithio thiadiazole products prepared in the preceding examples are added in varying amounts and to which comparative inhibitor components are added. The resultant formulations are subjected to the ASTM Copper Strip Corrosion Test (D 130-56). Briefly, this test comprises placing a polished copper strip in the test oil composition for a 3 hour period at 250°F. whereupon the degree of corrosive attach upon the strip is measured using a rating ranging from 1A to 4C with the rating of 1A representing the least corrosive attack and the rating of 4C representing the greatest corrosive attack.

In following Table I is a description of the base oil formulations:

TABLE I

| Ingredients | Wt. % Base Oil A | Wt. % Base Oil B |
|---|---|---|
| Paraffinic (1000 SUS at 100°F.) | 93.1 | 92.5 |
| Ethyloleyl Acid Phosphate | 1.0 | 1 |
| Sodium Sulfide Treated Diisobutylene Polysulfide* | 5.0 | — |
| Sulfurized Triisobutylene* | — | 5 |
| Terpolymer of butyl, lauryl, stearyl and dimethylaminoethyl methacrylates | 0.2 | 0.5 |
| Mixture of 2-mercaptobenzothiazole and t-$C_{18}$—$C_{22}$ alkylamine | 0.5 | — |
| Oleylamine | 0.2 | 1 |
| Dimethyl Silicone Antifoamant | 100 ppm | — |

*Extreme pressure agent corrosive to copper.

Table II below contains a description of the representative formulations of the invention and comparative formulations. Further, the formulations are compared basis the ASTM Copper Strip Corrosion Test as to their relative corrosiveness to copper, that is, the relative effectiveness of the copper corrosion inhibiting representative and comparative corrosion inhibiting additives in the hydrocarbon oil formulations.

TABLE II

Test Formulations and Copper Inhibitor Properties

| Run No. | Base Oil | Cu Corrosion Inhibitor | Inhibiting Conc. In Base Oil,Wt.% | Cu Strip Rating |
|---|---|---|---|---|
| 1 | A | Ex. III Prod. | .05 | 3A |
| 2 | A | Ex. III Prod. | 0.10 | 1B |
| 3 | A | 2,5-bis(t-octyl dithio)-1,3,4-thiadiazole* | .05 | 3B |
| 4 | A | Same | 0.1 | 1B |
| 5 | A | None | 0 | 4A |
| 6 | B | Ex. IV Prod. | 0.05 | 2E |
| 7 | B | Ex. IV Prod. | 0.10 | 2E |
| 8 | B | Ex. IV Prod. | 0.20 | 1B |
| 9 | B | 2,5-bis(t-octyl-dithio)-1,3,4-thiadiazole* | 0.05 | 2D |
| 10 | B | None | 0 | 4C |

*Commercial Inhibitor.

In the above Table II a comparison of the copper strip ratings of representative Runs 1, 2, 6, 7 and 8 with control Runs 5 and 10 demonstrate the effectiveness of the amino(hydrocarbyldithio)-thiadiazole products of the invention in inhibiting corrosion. Further, a comparison of representative Run Nos. 1, 2, 6, 7 and 8 with comparative Run Nos. 3 and 9 demonstrate that the thiadiazole products of the invention have an effectiveness of essentially the same quality as a widely used commercial corrosion inhibitor.

I claim:
1. As a new compound

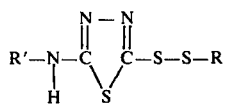

where R is alkyl, aryl, alkaryl or aralkyl of from 1 to 30 carbons and R' is hydrogen, alkyl, aryl, alkaryl or aralkyl of from 1 to 30 carbons and wherein said alkyl, aryl, alkaryl, and aralkyl are hydrocarbyl.

2. A compound in accordance with claim 1 wherein R is t-dodecyl and R' is hydrogen.

3. A compound in accordance with claim 1 wherein R is t-octyl and R' is hydrogen.

4. A compound in accordance with claim 1 wherein R is t-octyl and R' is ethyl.

* * * * *